(12) United States Patent
Czapla et al.

(10) Patent No.: US 11,219,499 B2
(45) Date of Patent: Jan. 11, 2022

(54) MEDICAL DEVICE HOLDER AND ASSEMBLY

(71) Applicant: M2 Medical Solutions, Inc., Avon, IN (US)

(72) Inventors: Mitchell Kenneth Czapla, Avon, IN (US); Matthew Christopher Nodley, Brazil, IN (US)

(73) Assignee: M2 MEDICAL SOLUTIONS, LLC, Avon, IN (US)

( * ) Notice: Subject to any disclaimer, the term of this patent is extended or adjusted under 35 U.S.C. 154(b) by 38 days.

(21) Appl. No.: 16/404,258

(22) Filed: May 6, 2019

(65) Prior Publication Data
US 2020/0138536 A1    May 7, 2020

Related U.S. Application Data

(60) Provisional application No. 62/756,226, filed on Nov. 6, 2018.

(51) Int. Cl.
*A61B 50/20* (2016.01)
*A61B 50/30* (2016.01)

(52) U.S. Cl.
CPC .............. *A61B 50/20* (2016.02); *A61B 50/30* (2016.02); *A61L 2202/182* (2013.01)

(58) Field of Classification Search
CPC ... A61B 50/20; A61B 50/30; A61L 2202/182; A61M 25/002
USPC ......................................... 206/370, 571, 363
See application file for complete search history.

(56) References Cited

U.S. PATENT DOCUMENTS

| | | | | |
|---|---|---|---|---|
| 5,339,955 | A | * | 8/1994 | Horan ..................... A61B 50/33 206/350 |
| 6,889,832 | B2 | * | 5/2005 | Gabele ...................... A61L 2/26 206/213.1 |
| 2015/0136719 | A1 | * | 5/2015 | Bally ..................... A61B 50/20 211/126.1 |
| 2016/0206394 | A1 | * | 7/2016 | Lampropoulos ....... A61B 50/30 |

* cited by examiner

*Primary Examiner* — J. Gregory Pickett
*Assistant Examiner* — Jenine Pagan
(74) *Attorney, Agent, or Firm* — Brannon Sowers & Cracraft PC

(57) ABSTRACT

A medical device holder includes a one-piece holder body having end walls, and side walls, extending vertically upward from a base. The end walls are oriented parallel to one another, and the first and the second side walls are oriented so as to converge toward one another in a direction of an opening. A plurality of medical device storage slots are formed by a plurality of internal vertical walls, and a plurality of elongate medical devices wound in opposition to an internal unwinding bias are trapped within the plurality of medical device storage slots.

17 Claims, 18 Drawing Sheets

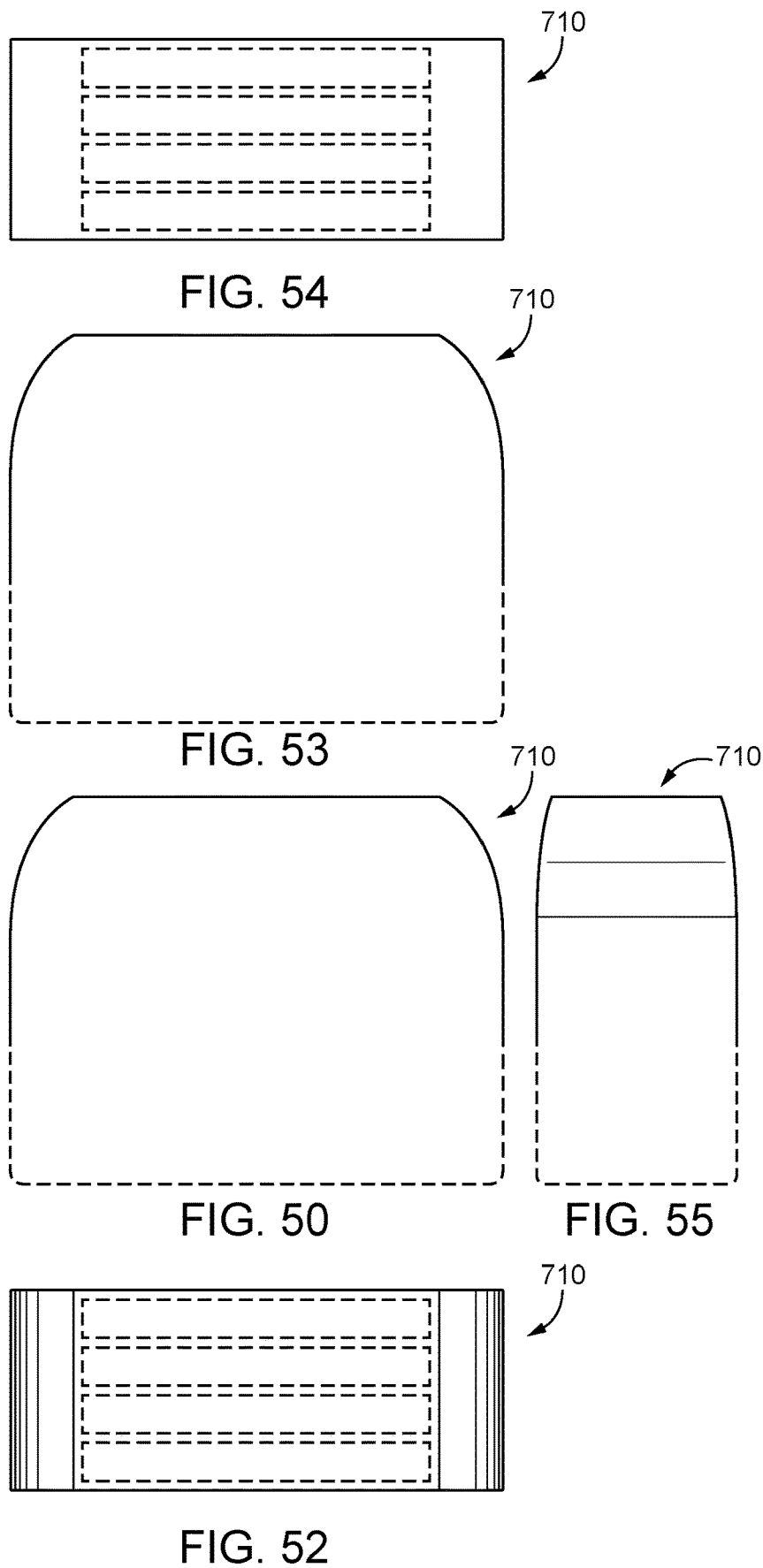

MEDICAL DEVICE HOLDER AND ASSEMBLY

CROSS-REFERENCE TO RELATED APPLICATIONS

The present application claims priority under 35 U.S.C. § 119(e) to U.S. Patent Provisional Application Ser. No. 62/756,226 filed Nov. 6, 2018.

TECHNICAL FIELD

The present disclosure relates generally to a holder for elongate flexible medical devices, and more particularly to a holder with medical device storage slots shaped to retain wound-up elongate medical devices wound in opposition to an internal unwinding bias.

BACKGROUND

A great many different medical devices are used in surgical and other clinical interventional settings. Elongate, flexible medical devices such as wire guides and catheters are often used by vascular surgeons, interventional radiologists, and other medical professionals to gain access to a patient's cardiovascular system, for diagnostics, imaging, and direct treatment of many conditions. Because such devices are often relatively long, in some instances over a meter, storing such devices such that they are prepared for ready and convenient access has long been a challenge. The necessity to maintain a sterile field compounds such problems, with a typical setting including placement of the long medical devices on a tray or table in the open air of the operating room or other clinical setting. Certain attempts have been made to provide purpose-built holding devices, however, conventional techniques and apparatuses for such purposes leave much to be desired.

SUMMARY OF THE INVENTION

In one aspect, a medical device holder includes a one-piece holder body with a horizontally extending base wall having a plurality of base peripheral edges extending about a planar base face and forming a base footprint, a first and a second end wall that extend vertically upward, respectively, from a first one and a second one of the plurality of base peripheral edges, and a first side wall and a second side wall that extend vertically upward, respectively, from a third one and a fourth one of the plurality of base peripheral edges. The medical device holder further includes an opening defined by a plurality of top peripheral edges each formed by a different one of the first and the second end walls and the first and the second side walls and forming an opening footprint that fits within the base footprint. The first and the second end walls are oriented parallel to one another, and the first and the second side walls are oriented so as to converge toward the opening. A plurality of internal vertical walls form a plurality of medical device storage slots serially arranged between the first and the second end walls and extending vertically between the opening and the base wall. The plurality of medical device storage slots further extend horizontally between the first and the second side walls and are shaped according to the convergence of the first and the second side walls so as to retain within the plurality of medical device storage slots a plurality of wound-up elongate medical devices inserted through the opening.

In another aspect, a medical device holder assembly includes a holder having a one-piece holder body with a horizontally extending base wall with a plurality of base peripheral edges extending about a planar base face, a first end wall and a second end wall extending vertically upward, respectively, from a first one and a second one of the plurality of base peripheral edges. The one-piece holder body further includes a first side wall and a second side wall extending vertically upward, respectively, from a third one and a fourth one of the plurality of base peripheral edges. The one-piece holder body further has a plurality of internal vertical walls forming a plurality of medical device storage slots extending between the first and the second side walls, and serially arranged between the first and the second end walls. The one-piece holder body further has a plurality of top peripheral edges each formed by a different one of the first and the second end walls and the first and the second side walls and defining an opening to the plurality of medical device storage slots. The first and the second end walls are oriented parallel to one another, and the first and the second side walls are oriented so as to converge toward one another in a direction of the opening. A plurality of elongate medical devices each wound in opposition to an internal unwinding bias are trapped each in a biased state by way of contact with the first and the second side walls and the base wall within one of the plurality of medical device storage slots.

BRIEF DESCRIPTION OF THE DRAWINGS

FIG. 50 is a left side view of the medical device holder design according to one embodiment;

FIG. 51 is a front view of the medical device holder shown in FIG. 50;

FIG. 52 is a top view of the medical device holder shown in FIG. 50;

FIG. 53 is a right side view of the medical device holder shown in FIG. 50;

FIG. 54 is a bottom view of the medical device holder shown in FIG. 50;

FIG. 55 is a back view of the medical device holder shown in FIG. 50;

DETAILED DESCRIPTION

Figure 1:
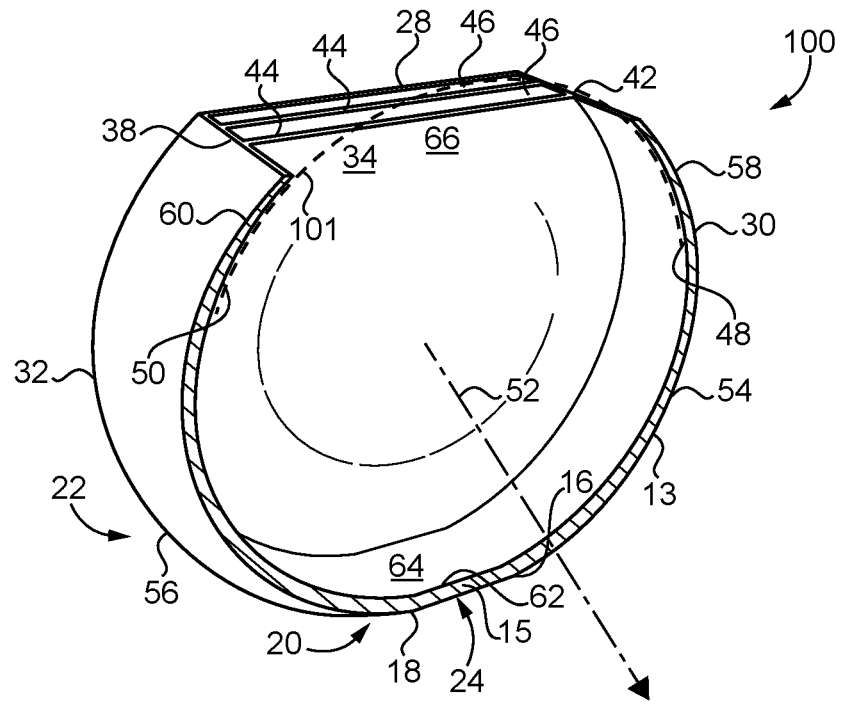
FIG. 1 is a sectioned diagrammatic view, in perspective, of a medical device holder, according to one embodiment.

Referring to the drawings, there are shown medical device holders according to several embodiments. Although described herein in the singular, the present description will be understood to refer generally to all embodiments except where otherwise indicated. Discussion herein of features or functionality of any one embodiment disclosed herein should be understood by way of analogy to refer to features or functionality of any other embodiment except where otherwise indicated or apparent from the context.

Figure 2:
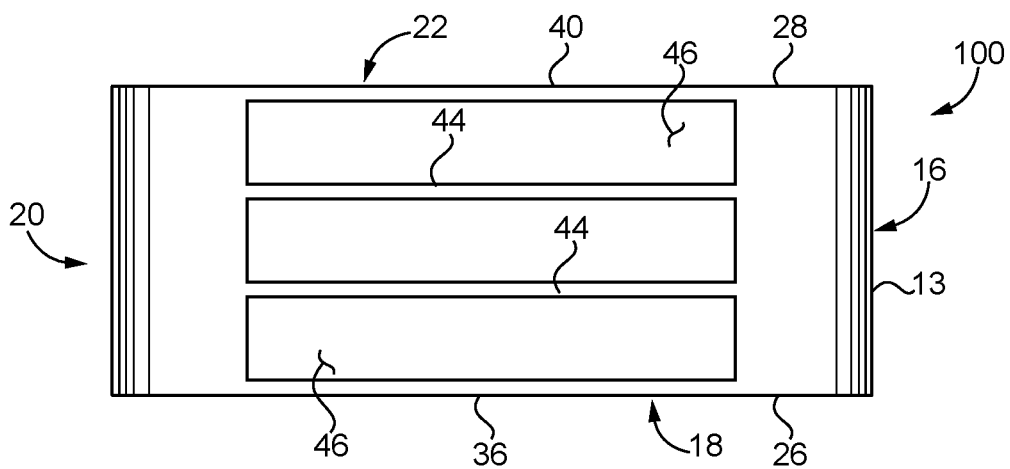
FIG. 2 is a top view of a medical device holder, according to one embodiment.

Medical device holder 100 (hereinafter "holder 100") shown in FIGS. 1-2 includes a one-piece holder body 13 having a horizontally extending base wall 15 with a plurality of base peripheral edges 16, 18, 20, and 22. The peripheral edges extend about a planar base face 24 and form a base footprint. It can be noted the base footprint has a generally rectangular shape thereby allowing the holder 100 to be stable on a flat surface. Holder body 13 further includes a first 26 and a second end wall 28 that extend vertically upward, respectively, from a first one and a second one of the plurality of base peripheral edges. Holder body 13 further includes a first side wall 30 and a second side wall 32 that extend vertically upward, respectively, from a third one and a fourth one of the plurality of base peripheral edges. In the embodiment of FIG. 1 first and second end walls 26 and 28 are substantially planar and extend vertically upward from base peripheral edges 18 and 22. First side wall 30 and second side wall 32 extend vertically upward from base peripheral edges 16 and 20. Holder body 13 can be formed, such as by so-called 3-D printing or another additive manufacturing process, from a medically suitable material such as an acrylonitrile butadiene styrene or another suitable polymeric material. As will be further apparent from the following description, holder 100 is uniquely configured for storing a plurality of elongate medical devices that can be wound-up into an annular form in opposition to an internal unwinding bias, and thereby trapped within holder 100 until such time as a clinician pulls the trapped elongate medical device out of holder 100 for use.

Device holder 100 further includes an opening 34 defined by a plurality of top peripheral edges 36, 38, 40, and 42 each formed by a different one of first and second end walls 26 and 28 and first and second side walls 30 and 32. Opening 34 forms an opening footprint that fits within the base footprint formed by the base peripheral edges. In an implementation, the opening footprint can be rectangular. First and second end walls 26 and 28 are oriented parallel to one another, and first and second side walls 30 and 32 are oriented so as to converge toward opening 34. In an implementation, each of side walls 30 and 32 includes a lower section 54 and 56 oriented perpendicular to planar base face 24, and an upper section 58 and 60 that follows a curve of a circle 101, as further discussed herein. First inner surface 48 may track a first arc of circle 101, with second inner surface 50 tracking a second arc of the circle. Other curvilinear or non-curvilinear shapes are contemplated herein that could be understood to converge in the manner described.

Holder body 13 further includes a plurality of internal vertical walls 44 forming a plurality of medical device storage slots 46 serially arranged between first and second end walls 26 and 28 and extending vertically between opening 34 and base wall 15. It can be noted that opening 34 can be understood to form, in profile, a chord of a circle defined by first and second side walls 30 and 32. The plurality of medical device storage slots 46 further extend horizontally between first and second side walls 30 and 32 and are shaped according to the convergence of the first and the second side walls so as to retain within the plurality of medical device storage slots 46 a plurality of wound-up elongate medical devices 70 inserted through opening 34.

The number of medical device storage slots can vary, and in a practical implementation may be from 3 to 100, potentially from 3 to 5. Slots could be identical to one another although the present disclosure is not thereby limited. Medical device storage slots define a common center axis 52 that extends through a center point of the circle forming the arcs tracked by first inner surface 48 of first side wall 30 and second inner surface 50 of second side wall 32. The opening footprint formed by opening 34 may be oriented parallel to the base footprint formed by peripheral edges 16, 18, 20, and 22. A third inner surface 62 is formed by base wall 15 and forms a bottom 64 of each one of medical device storage slots 46. Third inner surface 62 may be oriented parallel to planar base face 24. It can also be noted that third inner surface 62 can be understood to form another chord of the circle discussed herein.

Figure 3:
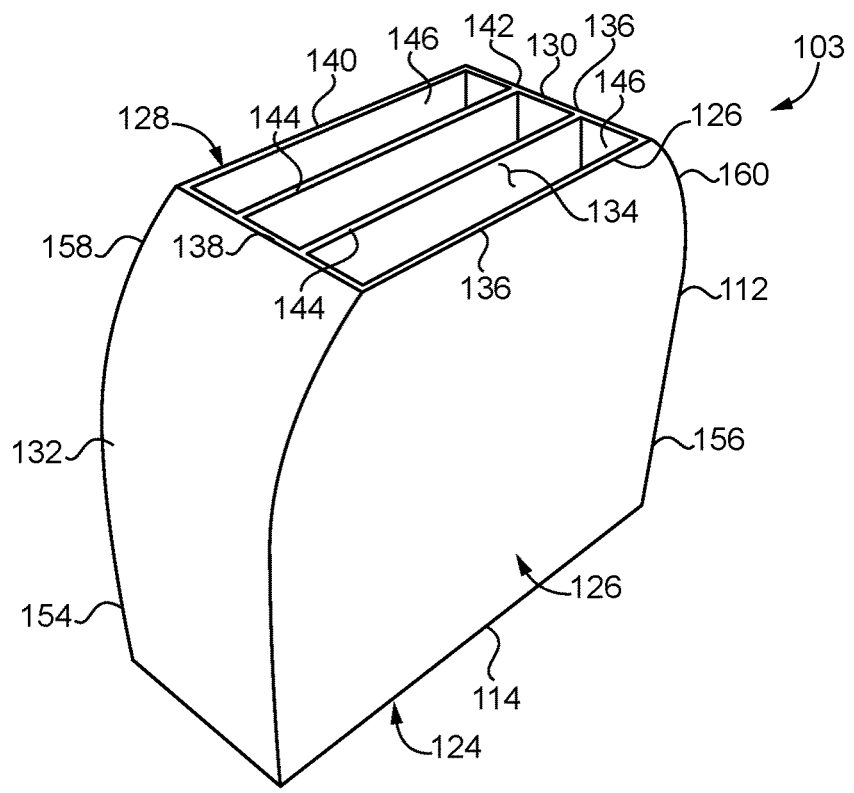
FIG. 3 is a diagrammatic view, in perspective, of a medical device holder, according to one embodiment.
Figure 4:
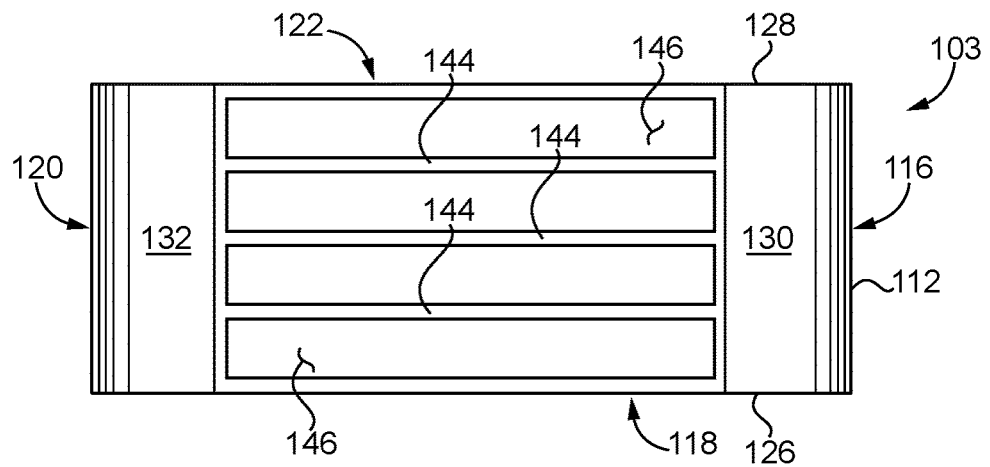
FIG. 4 is a top view of a medical device holder, according to one embodiment.

Referring to FIGS. 3-4, another example of a medical device holder 103 (hereinafter "holder 103") includes a one-piece holder body 112 having a horizontally extending base wall 114 with a plurality of base peripheral edges 116, 118, 120, and 122. The base peripheral edges extend about a planar base face 124 and form a base footprint, understood as a two-dimensional shape defined by base peripheral edges 116, 118, 120, and 122. It can be noted the base footprint has a generally rectangular shape thereby allowing the holder 103 to be stable on a flat surface. Holder body 112 further includes a first and a second end wall 126 and 128 that extend vertically upward, respectively, from a first one 118 and a second one 122 of the plurality of base peripheral edges. Holder body 112 further includes a first side wall 130 and a second side wall 132 that extend vertically upward, respectively, from a third one 116 and a fourth one 120 of the plurality of base peripheral edges. In the embodiment of FIGS. 3-4 first and second end walls 126 and 128 are substantially planar and extend vertically upward from the peripheral edges of base 114. First side wall 130 and second side wall 132 extend vertically upward from the peripheral edges of base 114. Holder body 112 can be formed, such as by so-called 3-D printing or another additive manufacturing process, from a medically suitable material such as an acrylonitrile butadiene styrene or another suitable polymeric material. As will be further apparent from the following description, holder 103 is uniquely configured for storing a plurality of elongate medical devices that can be wound-up into an annular form in opposition to an internal unwinding bias, and thereby trapped within holder 103 until such time as a clinician pulls the trapped elongate medical device out of holder 103 for use.

Device holder 103 further includes an opening 134 defined by a plurality of top peripheral edges 136, 138, 140, and 142 each formed by a different one of first and second end walls 126 and 128 and first and second side walls 130 and 132. Opening 134 forms an opening footprint, understood as a two-dimensional shape defined by top peripheral edges 136, 138, 140, and 142, that fits within the base footprint formed by the base peripheral edges. In an implementation, the opening footprint can be rectangular. First and second end walls 126 and 128 are oriented parallel to one another, and first and second side walls 130 and 132 are oriented so as to converge toward opening 134. In an implementation, each of side walls 130 and 132 includes a lower section 154 and 156 oriented perpendicular to base wall 114 and generally parallel to one another, and an upper section 158 and 160 that follows a curve of a circle, as further discussed herein. Other curvilinear or non-curvilinear shapes are contemplated herein that could be understood to converge in the manner described.

Holder body 112 further includes a plurality of internal vertical walls 144 forming a plurality of medical device storage slots 146 serially arranged between first and second end walls 126 and 128 and extending horizontally from first side wall 130 to second side wall 132 and vertically between opening 134 and base wall 114. It can be noted that opening 134 can be understood to form, in profile, a chord of a circle defined by the upper sections upper section 158 and 160 of first and second side walls 130 and 132. The plurality of medical device storage slots 146 further extend horizontally between first and second side walls 130 and 132 and are shaped according to the convergence of the first and the second side walls so as to retain within the plurality of medical device storage slots 146 a plurality of wound-up elongate medical devices inserted through opening 134.

Figure 5:
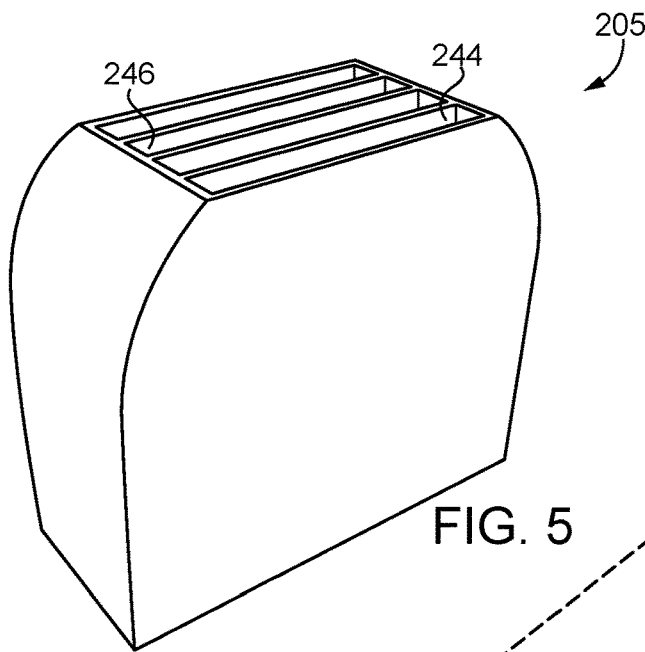
FIG. 5 is a diagrammatic view, in perspective, of a medical device holder, according to one embodiment.
Figure 7:
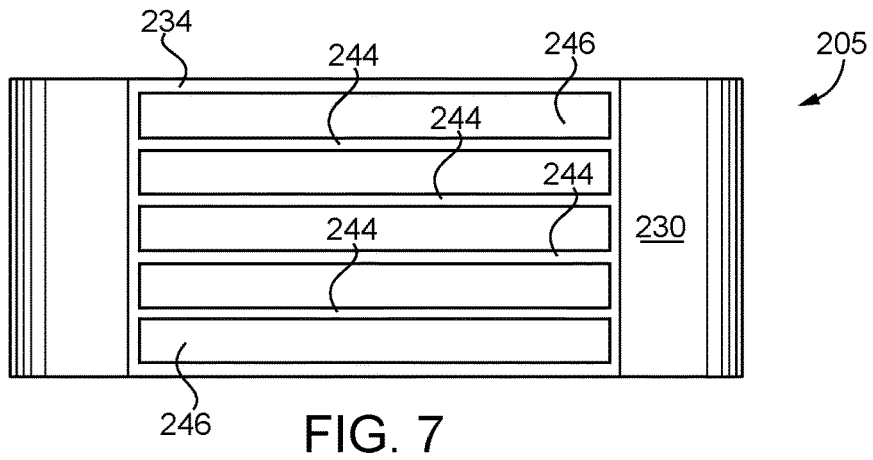
FIG. 7 is a top view of a medical device holder, according to one embodiment.

Another example of a medical device holder is shown in FIGS. 5 and 7 similar to the example shown in FIGS. 3-4. In this particular example, a holder 205 includes an opening 234 which is divided into five medical device storage slots 246 by four internal vertical walls 244 rather than the four slots and three internal vertical walls as shown in FIGS. 3-4.

Figure 6:
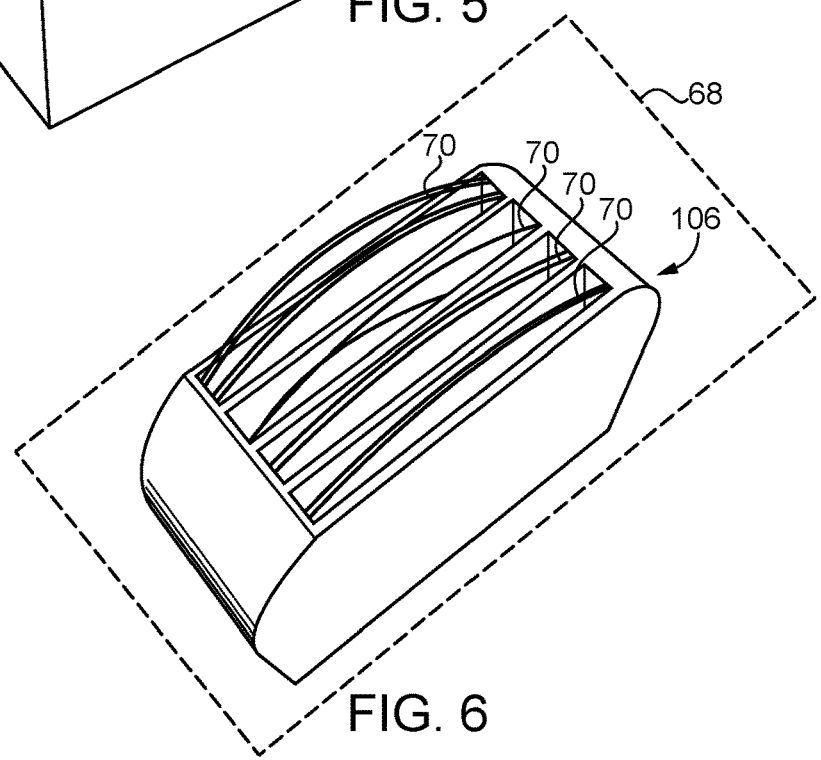
FIG. 6 is a diagrammatic view, in perspective, of a medical device holder assembly, according to one embodiment.

FIG. 6 shows a plurality of elongate medical devices 70 as they might appear positioned within storage slots as described herein. An assembly of holder 106 and elongate medical devices 70, or holder 106 by itself, can be positioned within a sterile storage envelope 68 of generally conventional construction. A number of medical device storage slots can vary, and in a practical implementation may be from 3 to 100, potentially from 3 to 5. Slots could be identical to one another although the present disclosure is not thereby limited. For example, slots or other storage compartments other than those described herein might also be included as part of a medical device holder so as to store other medical devices used in a particular procedure in a single medical device holder.

Figure 8:
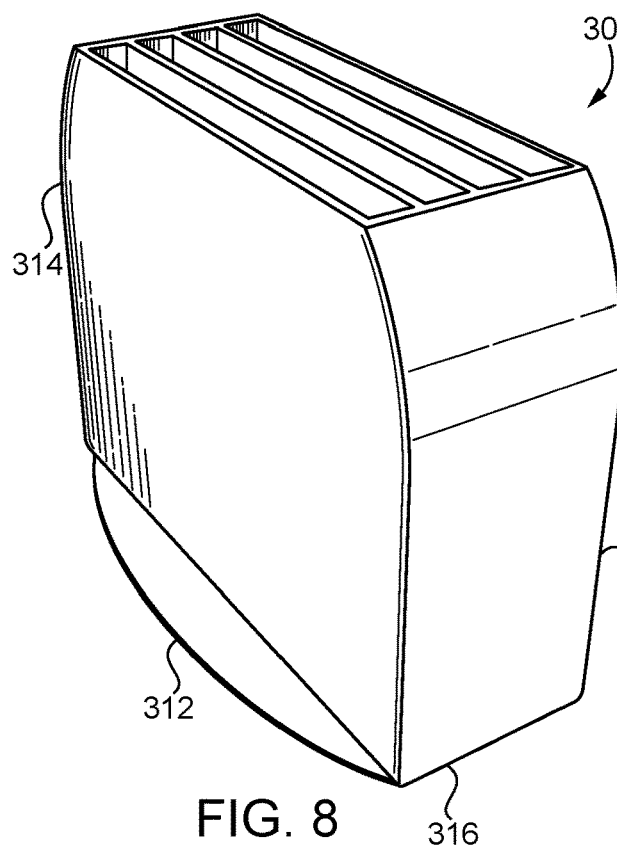
FIG. 8 is a perspective view of a medical device holder, according to another embodiment.
Figure 9:
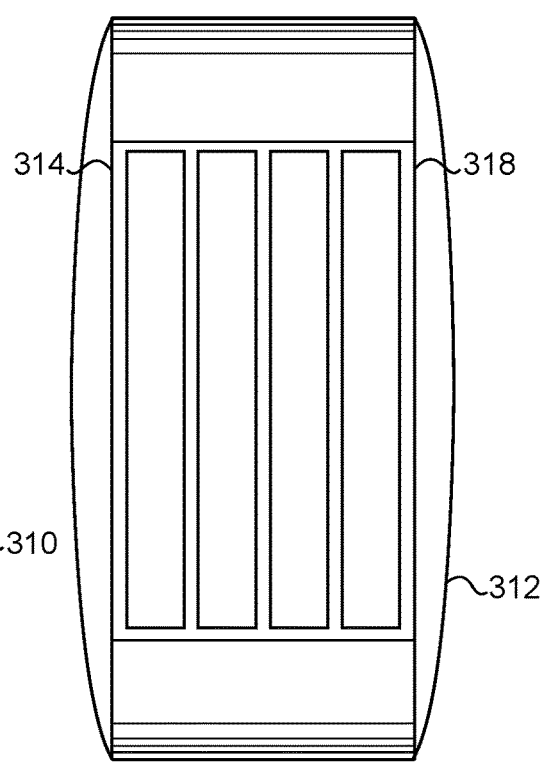
FIG. 9 is a top plan view of the medical device holder shown in FIG. 8.
Figure 10:
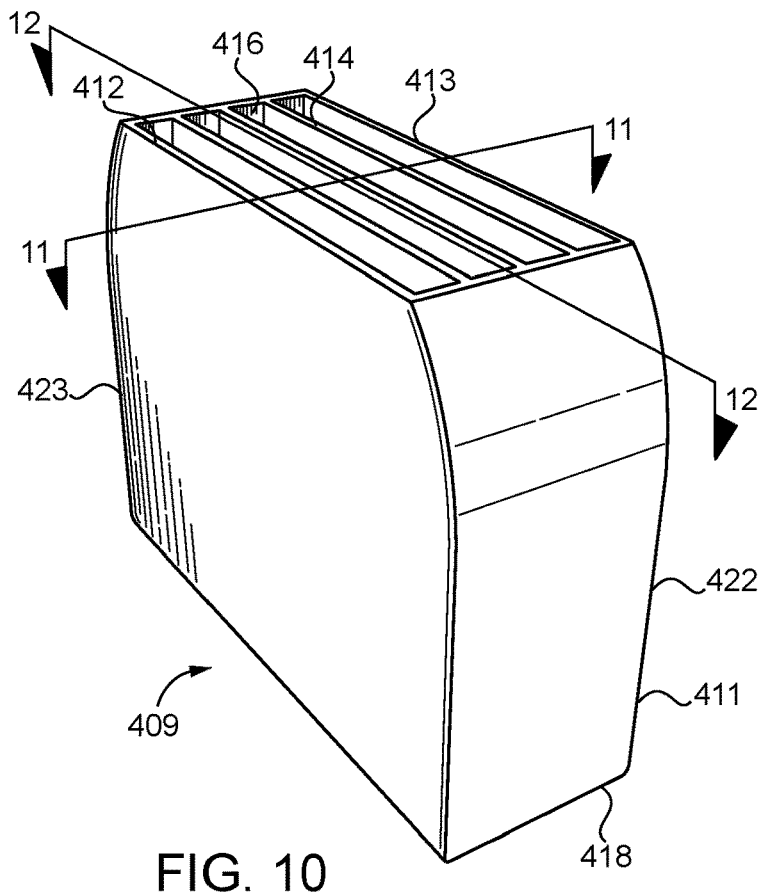
FIG. 10 is a perspective view of a medical device holder according to still another embodiment.

In the example shown in FIGS. 8-9, a medical device holder 308 similar to those depicted in FIGS. 3-5 and 7 is shown. In this particular example, holder 308 includes a one-piece holder body 310 having a horizontally extending base wall 316. A base stabilizer 312 is attached to the base wall 316 and extends beyond the plane of a first end wall 314 and a second end wall 318. The base stabilizer 312 as shown in this particular example has generally curved edges, but in other examples different shapes, sizes, and configurations of base stabilizers may be used. In still other examples, a base stabilize may extend beyond the side walls of the holder. A base stabilizer may be configured so as to lockably engage with a surface to provide additional stability or include one or more magnets for the same purpose.

Figure 12:
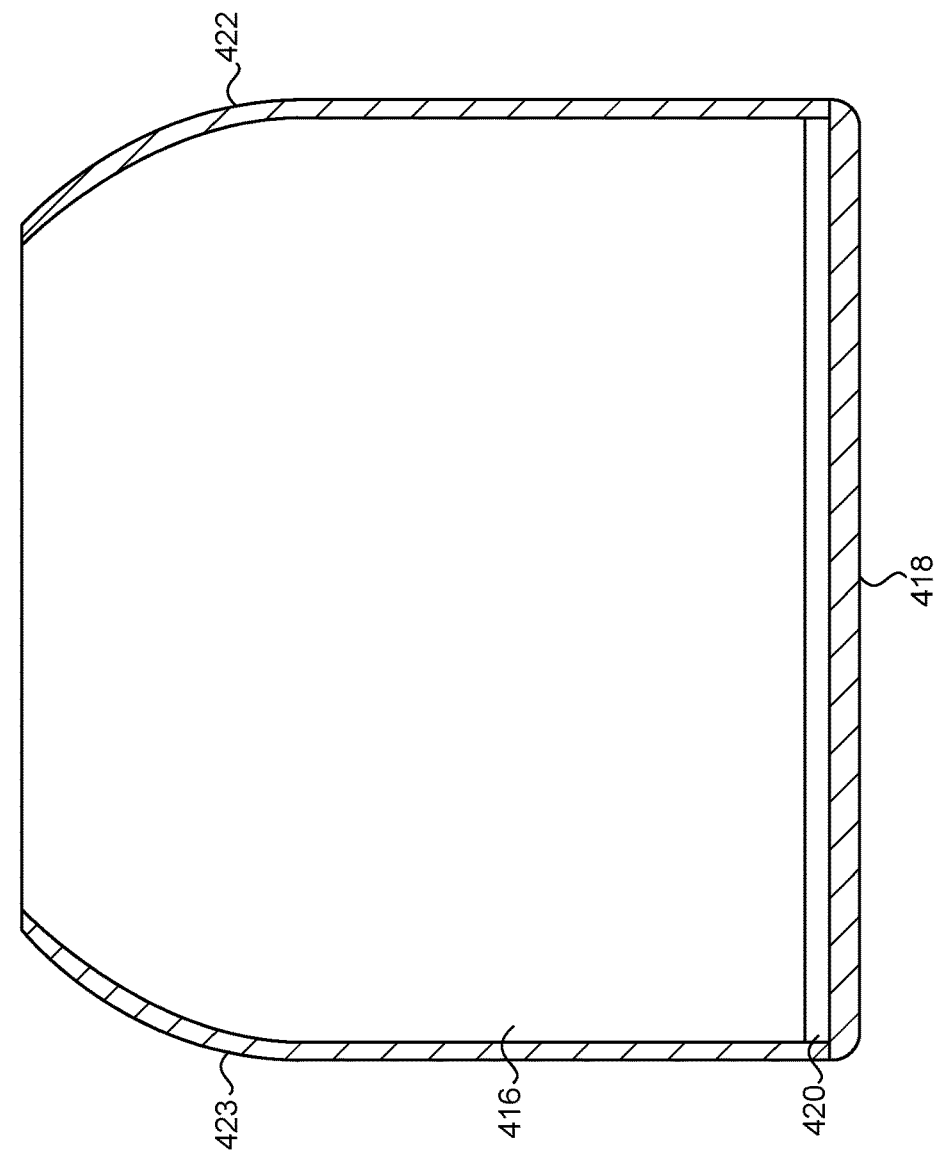
FIG. 12 is a partial cross sectional view of the medical device holder of FIG. 10 along line 12-12.
Figure 11:
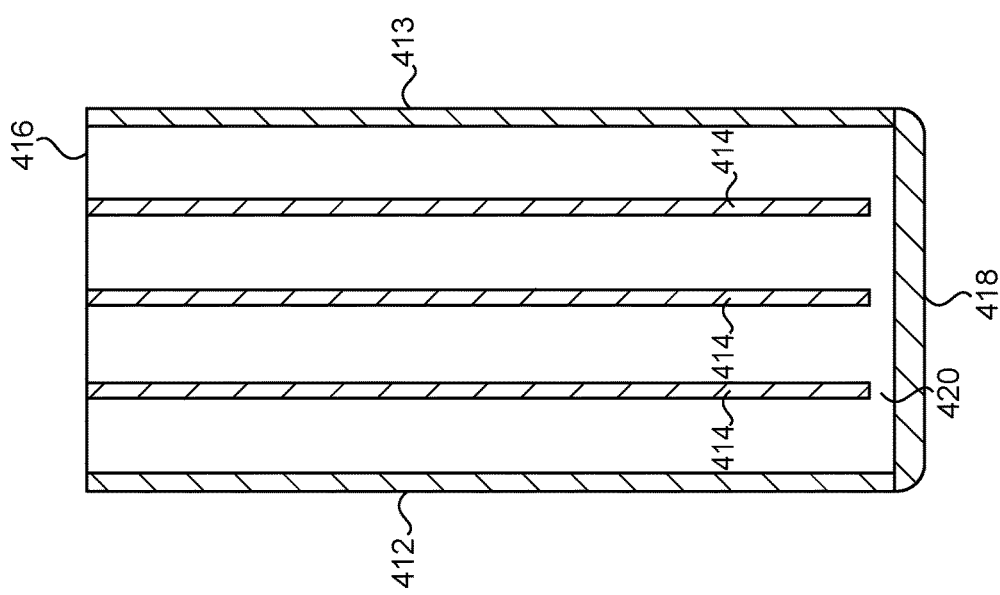
FIG. 11 is a cross sectional view of the medical device holder of FIG. 10 along line 11-11.

FIGS. 10-13 show another example of a medical device holder 409. In this example, the holder 409 includes a one-piece holder body 411 having a horizontally extending base wall 418, a first and second end wall 412 and 413, and a first and second side wall 422 and 423 which extend vertically from base wall 418. The interior of body 411 is divided into four slots 416 by three internal walls 414. As shown in FIGS. 11-12, internal walls 414 are attached to side walls 422 and 423 but not to base 418 which creates a gap 420 at the bottom of each internal wall 414 allowing for fluidic communication between each of the slots 416. The exact size of gap 420 can vary as desired. In other examples, one or more slots may be separated or not in fluidic communication with one or more slots which are in fluidic communication with one another.

Figure 13:
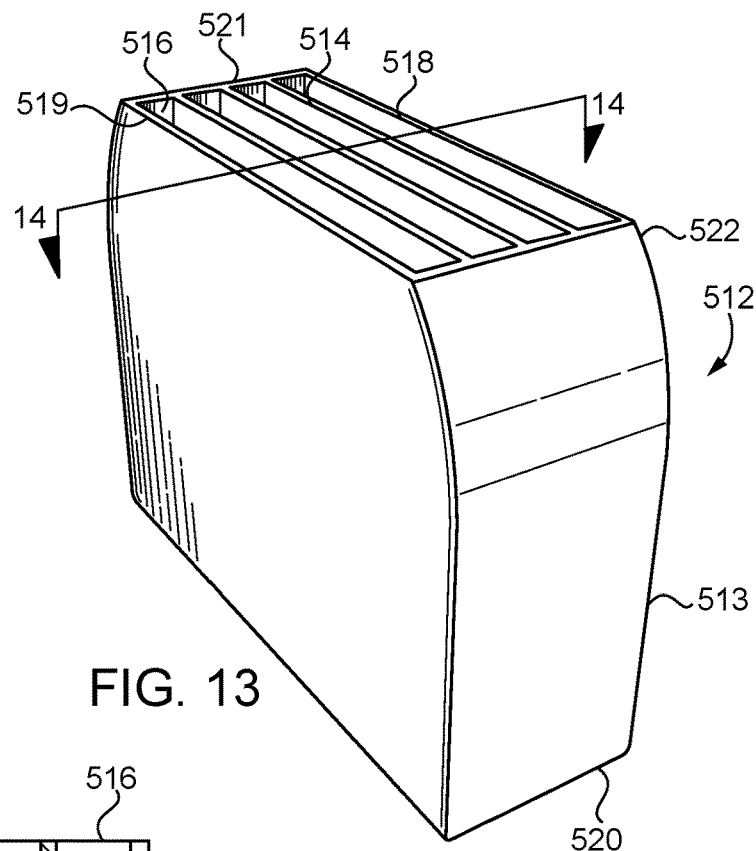
FIG. 13 is a perspective view of a medical device holder according to a further embodiment.
Figure 14:
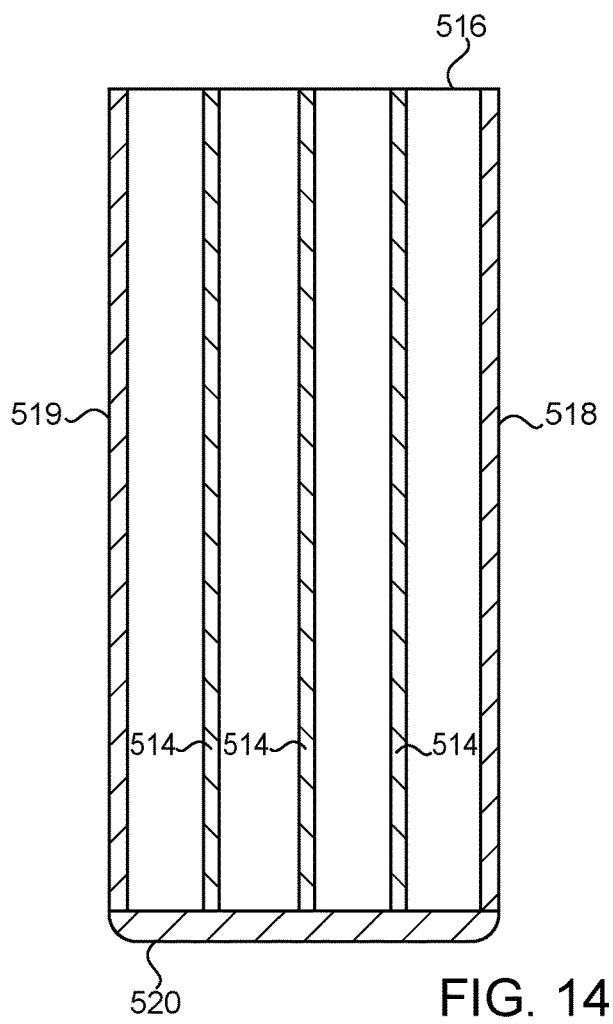
FIG. 14 is a cross sectional view of the medical device holder of FIG. 13 along line 14-14.

Another example of a medical device holder 512 is shown in FIGS. 13-14. A holder 512 includes a one-piece holder body 513 having a horizontally extending base wall 520, a first and second end wall 518 and 519, and a first and second side wall 521 and 522 which extend vertically from base wall 520. The interior of body 513 is divided into four slots 516 by three internal walls 514. As shown in FIG. 14, internal walls 514 are attached to base 520 which isolates each slot 516 from one another and prevents fluidic communication therebetween.

Figure 15:
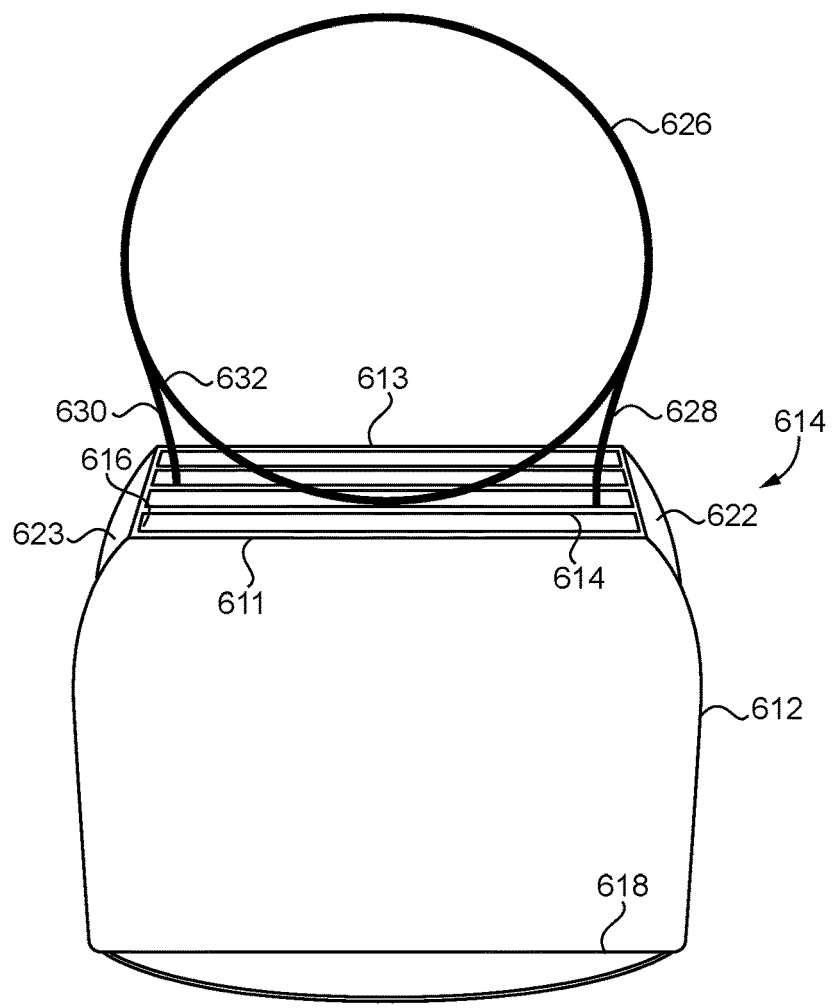
FIG. 15 is a perspective view of a medical device holder according to an embodiment.
Figure 16:
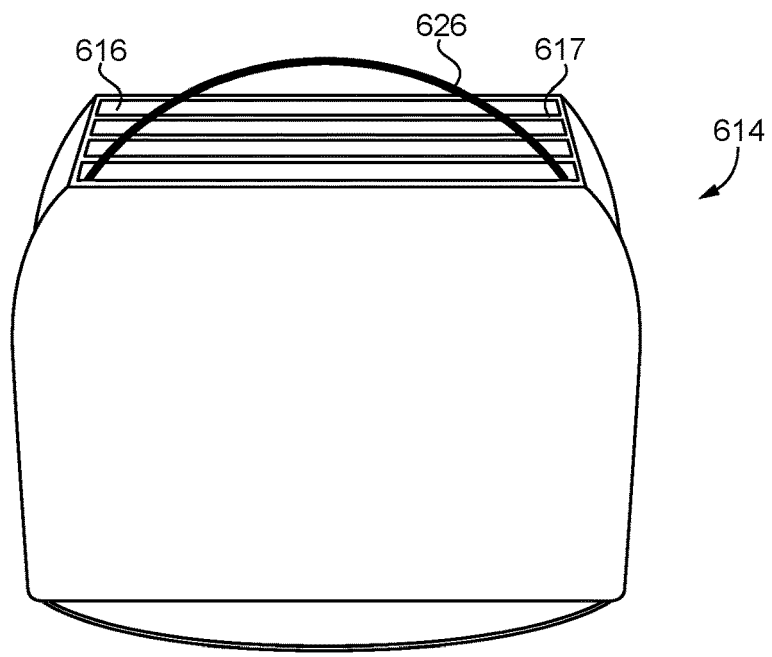
FIG. 16 is a perspective view of the medical device holder of FIG. 15.
Figure 17:
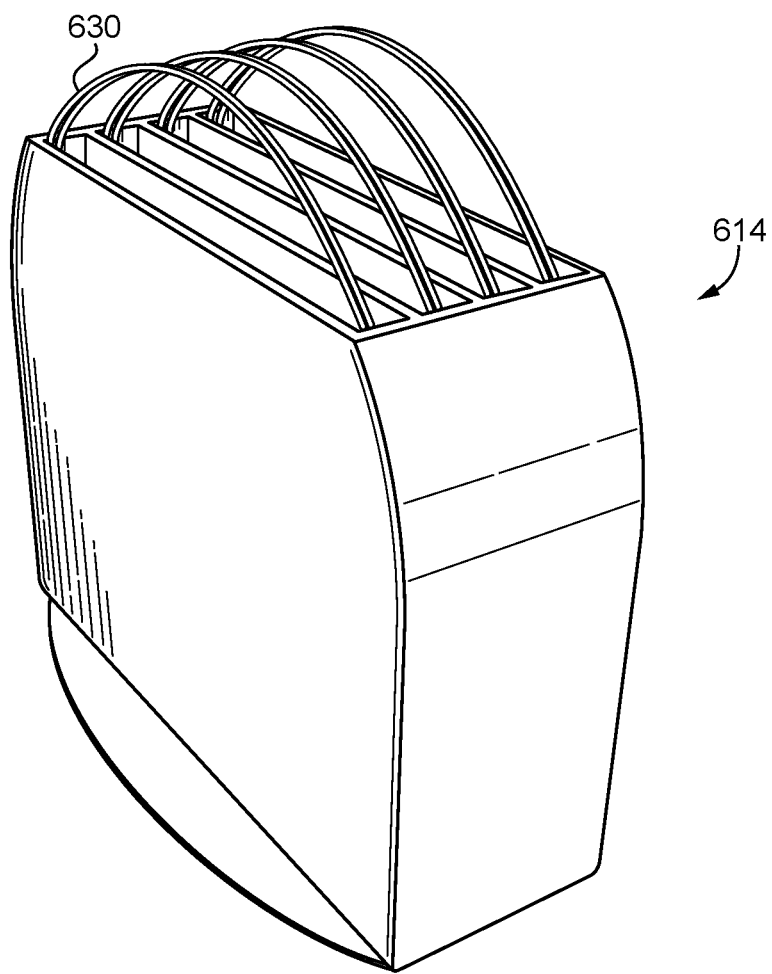
FIG. 17 is another perspective view of the medical device holder of FIG. 15.
Figure 22:
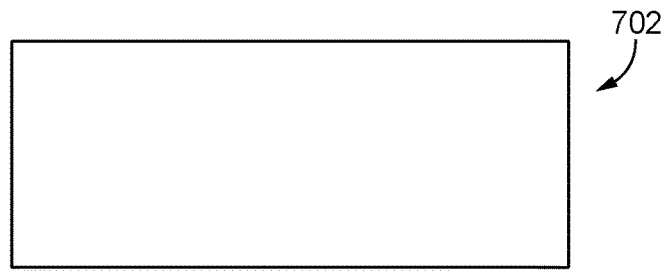
FIG. 22 is a bottom view of the medical device holder shown in FIG. 18.
Figure 21:
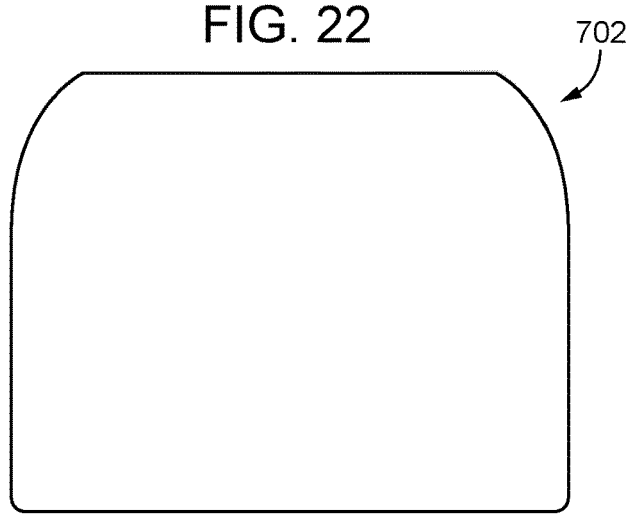
FIG. 21 is a right side view of the medical device holder shown in FIG. 18.
Figure 19:
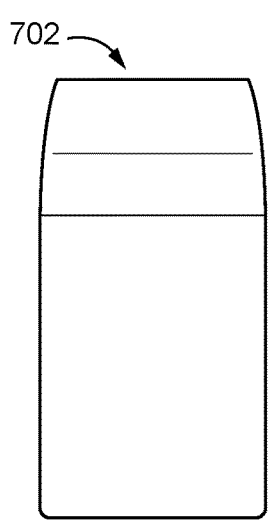
FIG. 19 is a front view of the medical device holder shown in FIG. 18.
Figure 18:
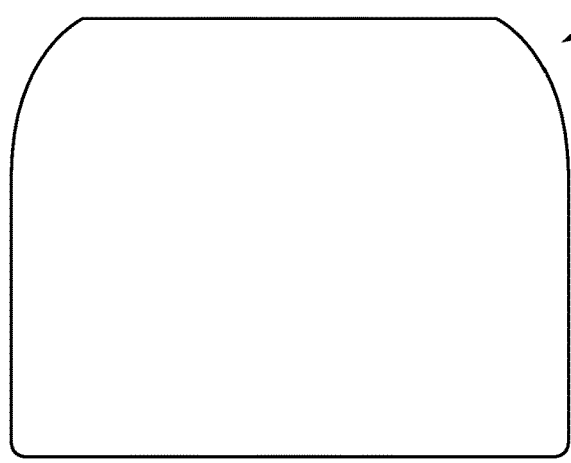
FIG. 18 is a left side view of the medical device holder design according to one embodiment.
Figure 23:
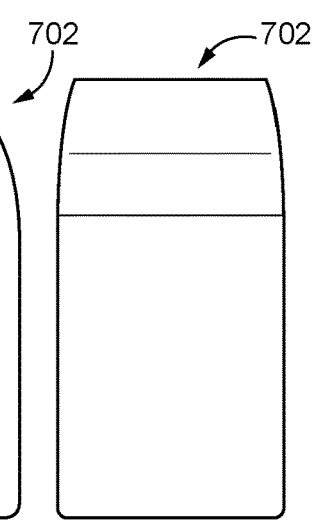
FIG. 23 is a back view of the medical device holder shown in FIG. 18.
Figure 20:
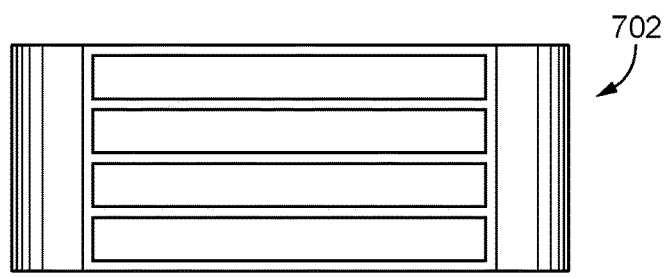
FIG. 20 is a top view of the medical device holder shown in FIG. 18.
Figure 24:
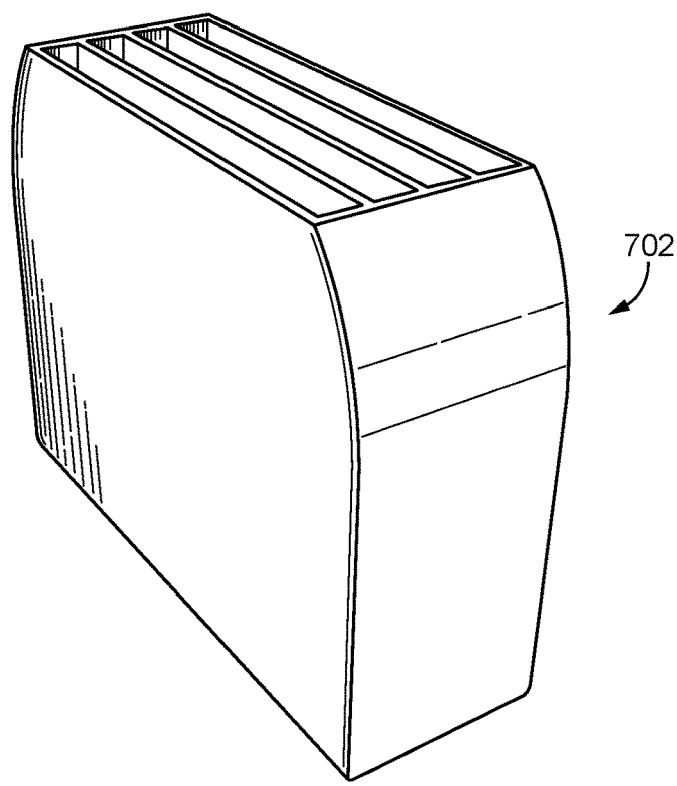
FIG. 24 is a perspective view of the medical device holder shown in FIG. 18.
Figure 25:
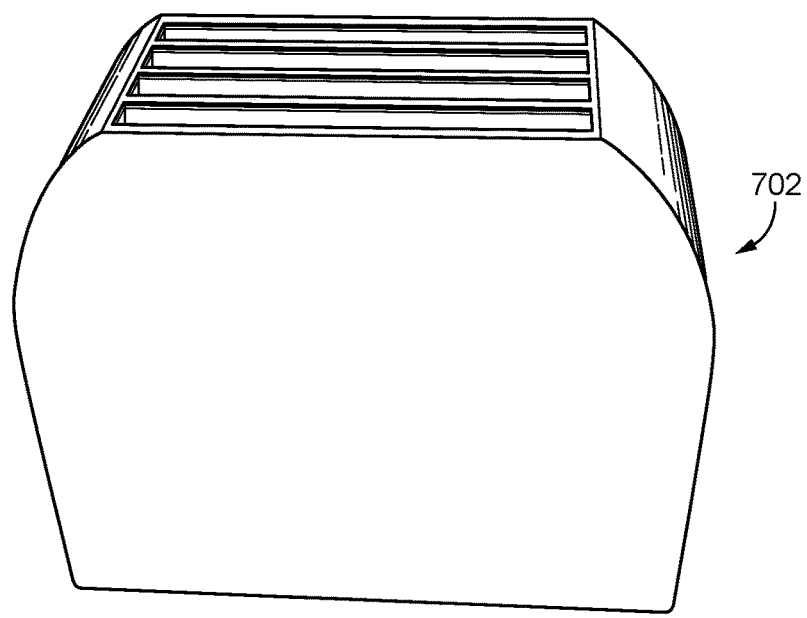
FIG. 25 is a perspective view of the medical device holder shown in FIG. 18.
Figure 30:
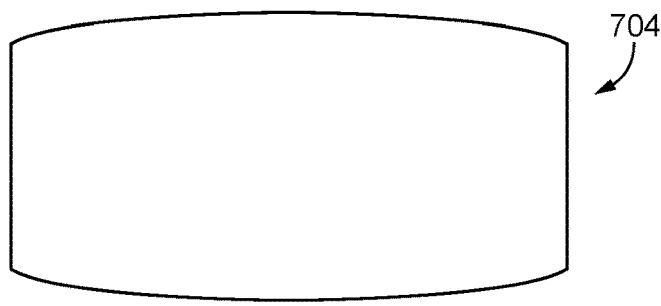
FIG. 30 is a bottom view of the medical device holder shown in FIG. 26.
Figure 29:
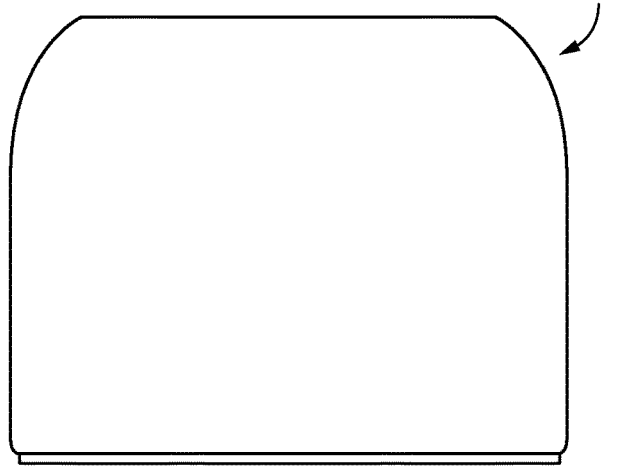
FIG. 29 is a right side view of the medical device holder shown in FIG. 26.
Figure 27:
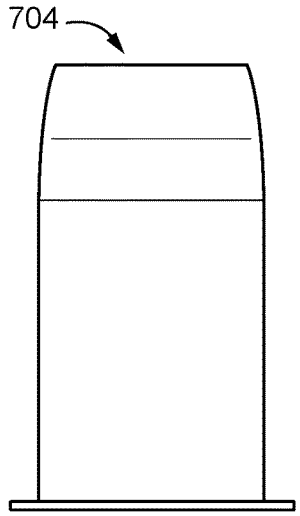
FIG. 27 is a front view of the medical device holder shown in FIG. 26.
Figure 26:
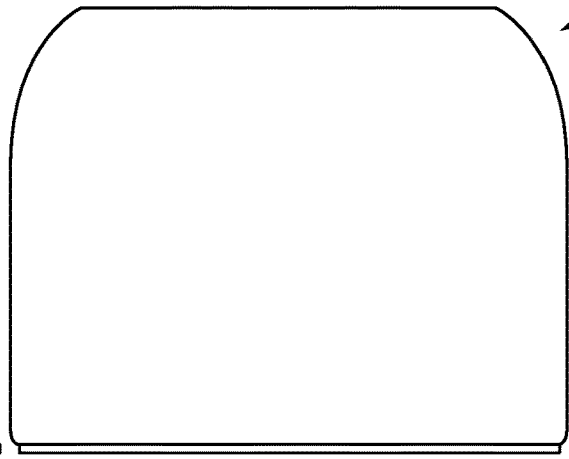
FIG. 26 is a left side view of the medical device holder design according to one embodiment.
Figure 31:
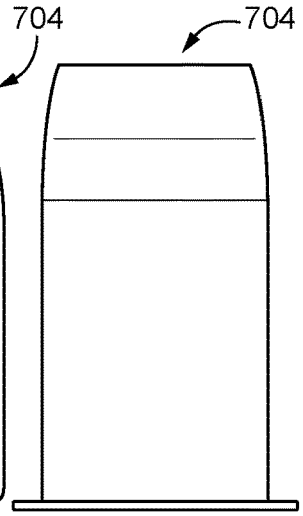
FIG. 31 is a back view of the medical device holder shown in FIG. 26.
Figure 28:
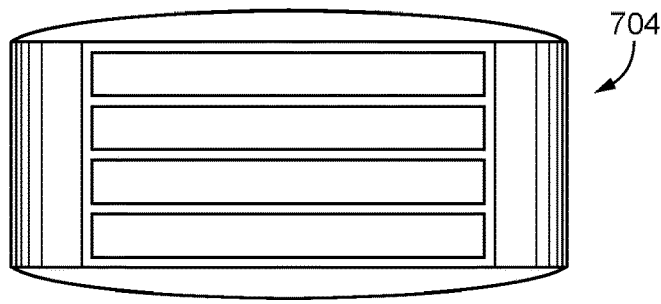
FIG. 28 is a top view of the medical device holder shown in FIG. 26.
Figure 32:
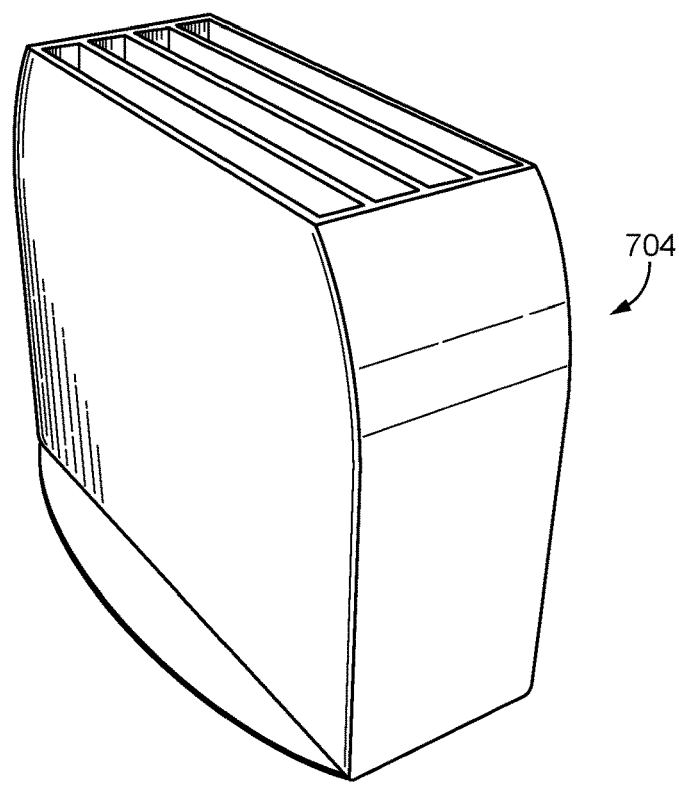
FIG. 32 is a perspective view of the medical device holder shown in FIG. 26.
Figure 33:
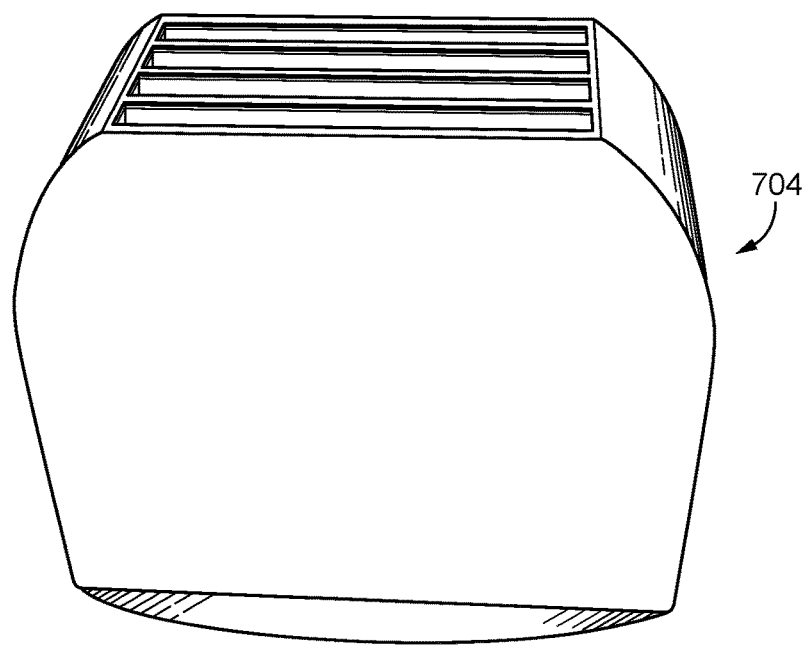
FIG. 33 is a perspective view of the medical device holder shown in FIG. 26.
Figure 38:
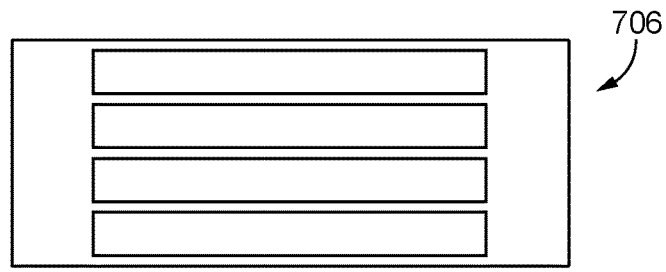
FIG. 38 is a bottom view of the medical device holder shown in FIG. 34.
Figure 37:
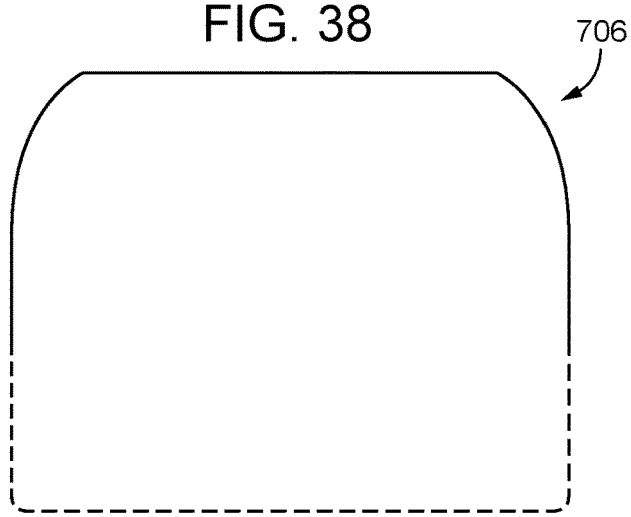
FIG. 37 is a right side view of the medical device holder shown in FIG. 34.
Figure 35:
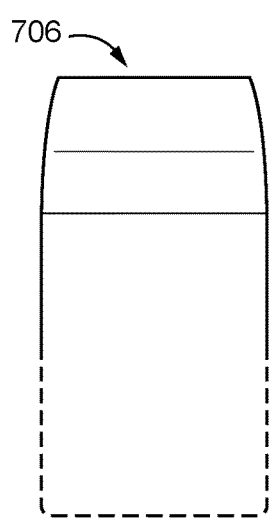
FIG. 35 is a front view of the medical device holder shown in FIG. 34.
Figure 34:
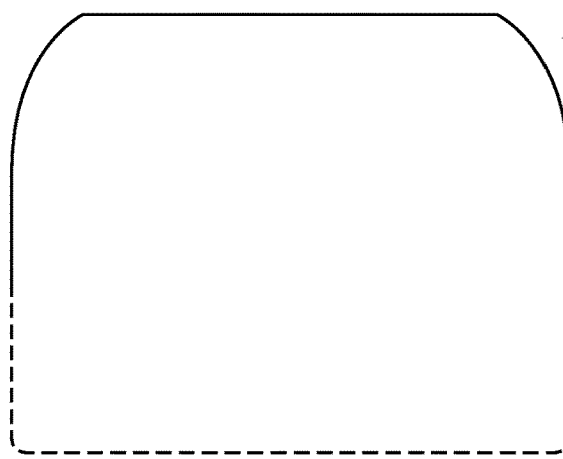
FIG. 34 is a left side view of the medical device holder design according to one embodiment.
Figure 39:
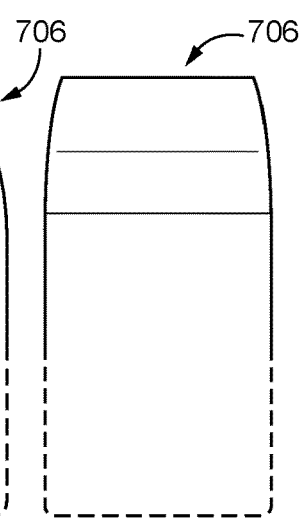
FIG. 39 is a back view of the medical device holder shown in FIG. 34.
Figure 36:
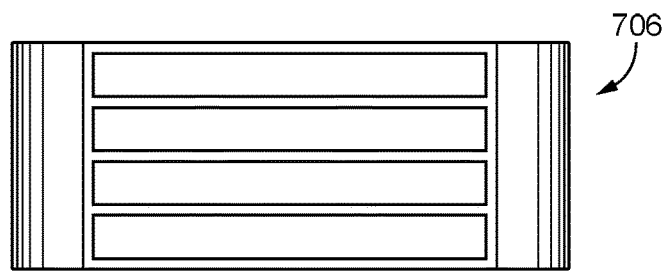
FIG. 36 is a top view of the medical device holder shown in FIG. 34.
Figure 40:
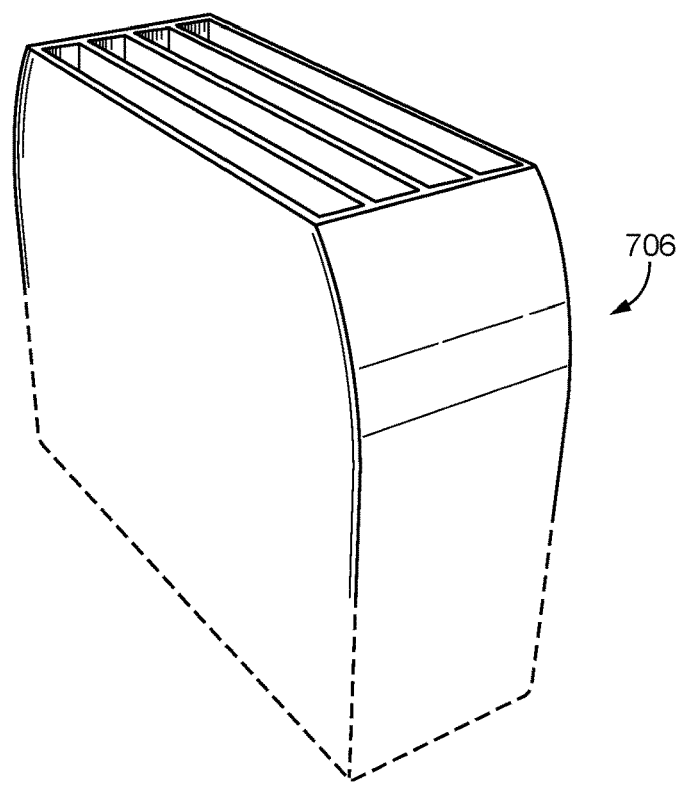
FIG. 40 is a perspective view of the medical device holder shown in FIG. 34.
Figure 41:
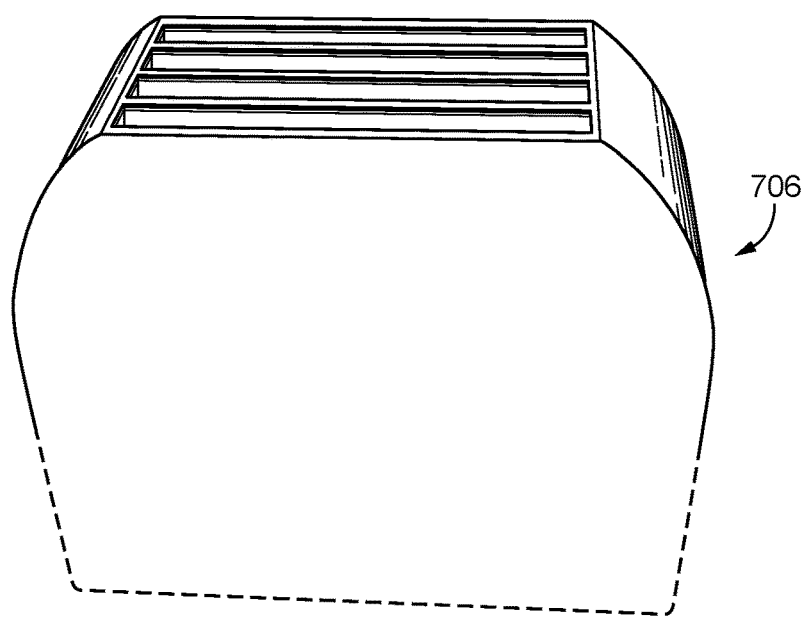
FIG. 41 is a perspective view of the medical device holder shown in FIG. 34.
Figure 46:
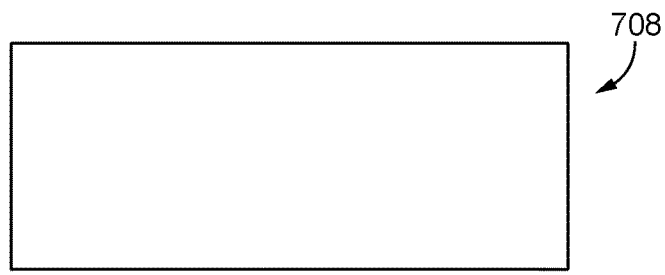
FIG. 46 is a bottom view of the medical device holder shown in FIG. 42.
Figure 45:
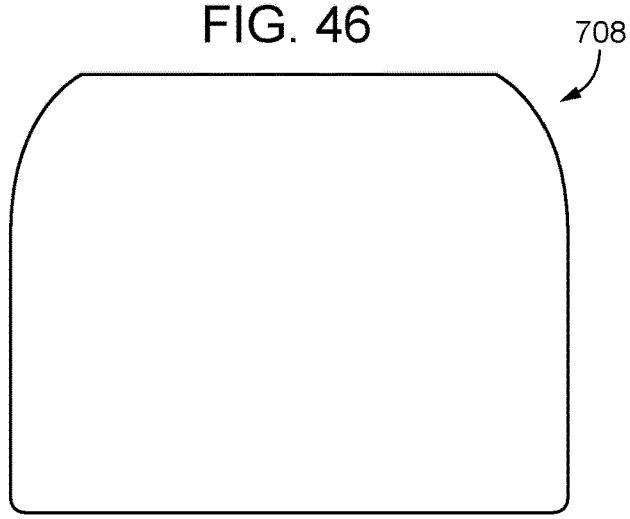
FIG. 45 is a right side view of the medical device holder shown in FIG. 42.
Figure 43:
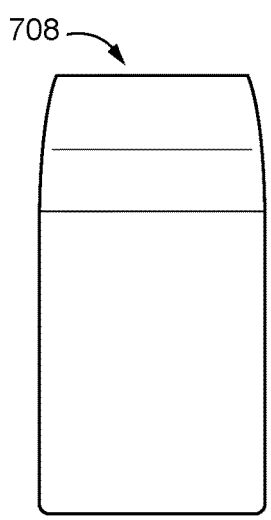
FIG. 43 is a front view of the medical device holder shown in FIG. 42.
Figure 42:
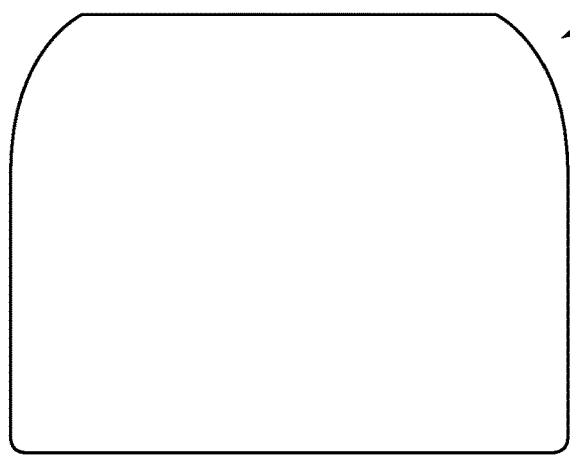
FIG. 42 is a left side view of the medical device holder design according to one embodiment.
Figure 47:
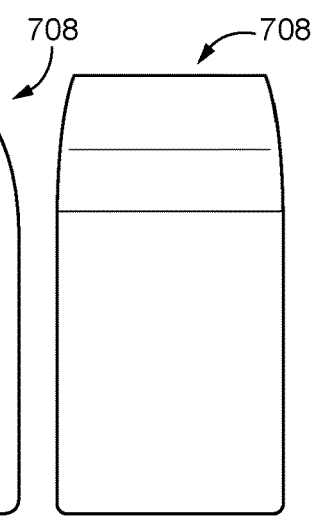
FIG. 47 is a back view of the medical device holder shown in FIG. 42.
Figure 44:
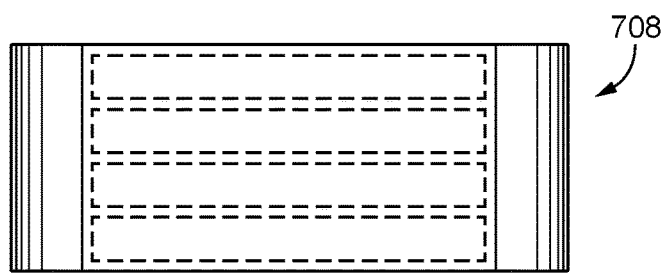
FIG. 44 is a top view of the medical device holder shown in FIG. 42.
Figure 48:
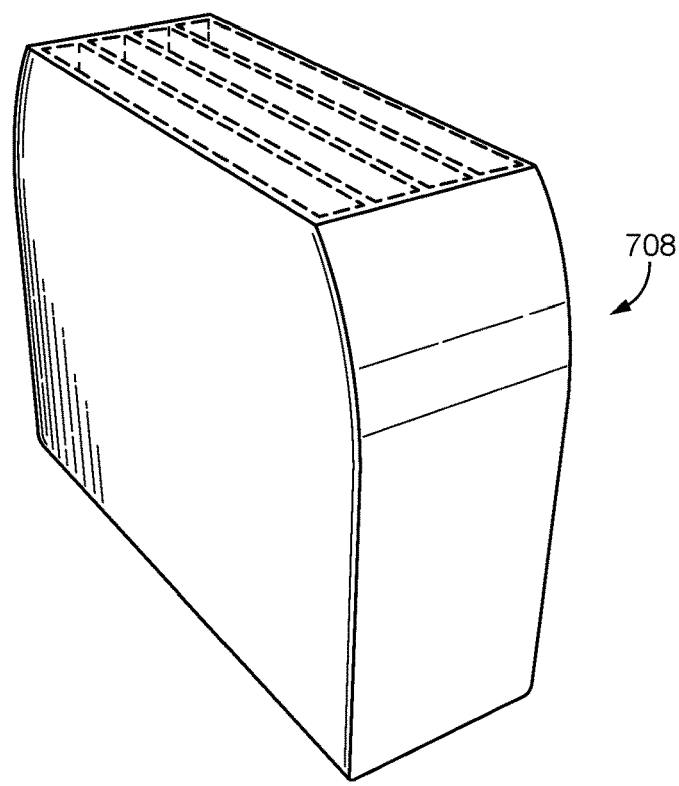
FIG. 48 is a perspective view of the medical device holder shown in FIG. 42.
Figure 49:
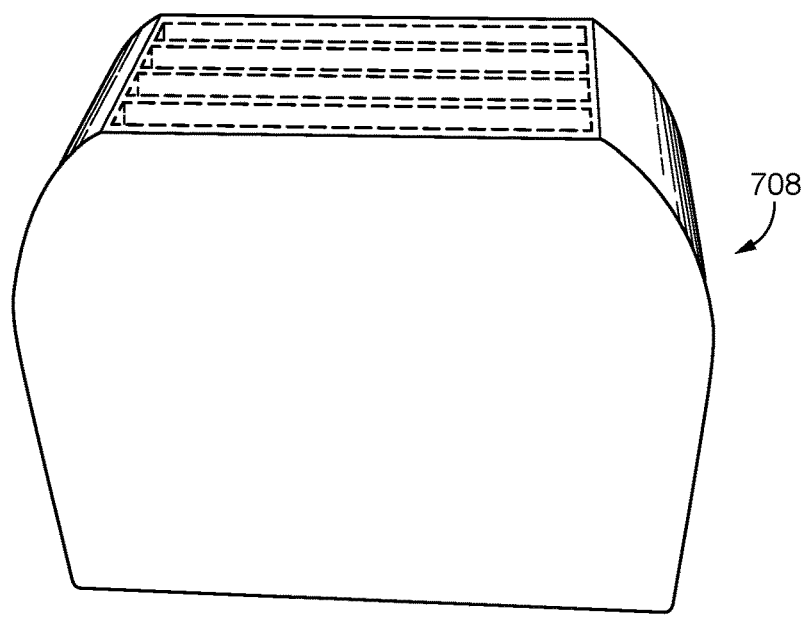
FIG. 49 is a perspective view of the medical device holder shown in FIG. 42.
Figure 56:
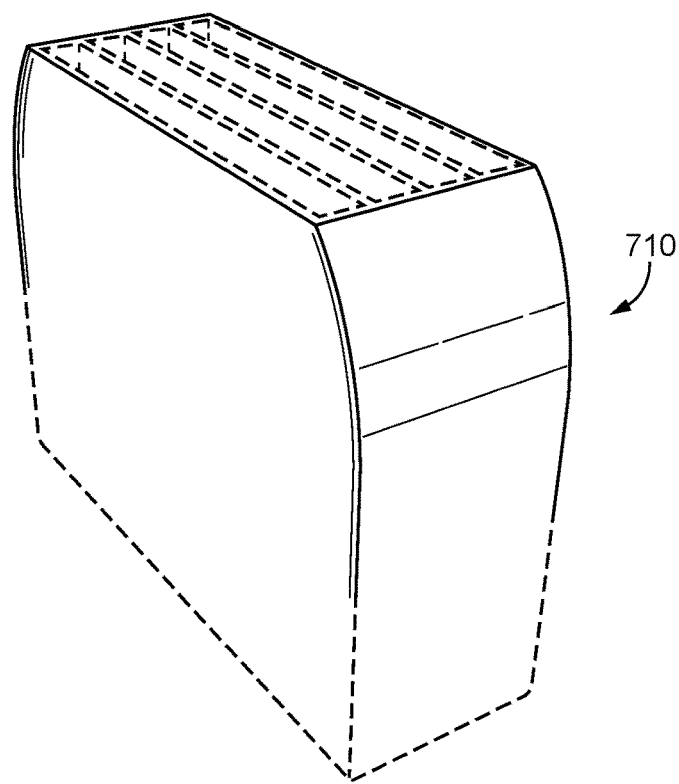
FIG. 56 is a perspective view of the medical device holder shown in FIG. 50.
Figure 57:
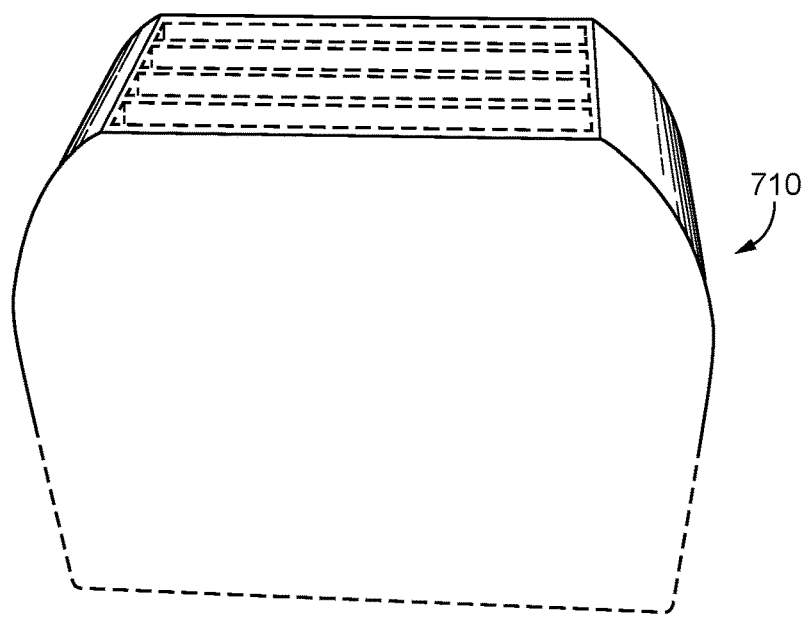
FIG. 57 is a perspective view of the medical device holder shown in FIG. 50.

FIGS. 15-17 show another example of a medical device holder 614 which includes a one-piece holder body 612 having a horizontally extending base wall 618, a first and second end wall 611 and 613, and a first and second side wall 622 and 623 which extend vertically from base wall 618. The interior of body 612 is divided into four slots 416 defined by three internal walls 617, the first and second end wall 611 and 613, and the first and second side wall 622 and 623. An elongate medical device 632 such as a catheter having a first end 628 and a second end 630 may be wound in opposition to an internal unwinding bias so as to form one or more coils 626. The coiled medical device 632 may then be inserted into a slot 616 where it is trapped in a biased state by contact with the first and second side wall 622 and 623 and the base wall 618, thereby holding the medical device 632 within the medical device holder 614 until such time as it is needed and removed by a clinician. In this example, the medical device is a catheter wire, but other elongate medical devices may also be stored and deployed from medical device holders as disclosed herein.

FIGS. 18-57 show other embodiments of medical device holders according to the present disclosure. It should be understood that the features and functionality of these embodiments is similar to those embodiments discussed above except where otherwise indicated or apparent from context. FIGS. 18-25 disclose a medical device holder 702 according to one embodiment of the present disclosure. FIGS. 26-33 disclose a medical device holder 704 according to another embodiment of the present disclosure. FIGS. 34-41 disclose a medical device holder 706 according to still another embodiment of the present disclosure. FIGS. 42-49 disclose a medical device holder 708 according to a further embodiment of the present disclosure. FIGS. 50-57 disclose a medical device holder 710 according to yet another embodiment of the present disclosure.

INDUSTRIAL APPLICABILITY

As discussed above, medical professionals have for many years struggled with preparing and positioning certain elongate medical devices such as wire guides and catheters for convenient access while maintaining a sterile environment. The present disclosure is contemplated to provide a relatively simple and straightforward mechanism for storing elongate medical devices for use. In some instances it is desirable to soak such medical devices in liquid solutions such as saline and/or solutions containing heparin, or still other liquid solutions. One or more of medical device storage slots could be filled with a suitable liquid for such purposes. Optionally, multiple slots could be in fluidic communication with one another to facilitate filling multiple slots with the same liquid. In other examples, slots could be fluidically isolated so that different devices stored in the same medical device holder could be soaked in different liquids. The disclosed medical storage devices may be preloaded with one or more medical devices (e.g., catheters) and then the storage device sealed in a sterile packaging material. Such sterile packaging is known in the industry.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims. As used herein, the articles "a" and "an" are intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:
1. A medical device holder comprising:
a one-piece holder body including a horizontally extending base wall having a plurality of base peripheral edges extending about a planar base face and forming a base footprint, a first and a second end wall that extend vertically upward, respectively, from a first one and a second one of the plurality of base peripheral edges, and a first side wall and a second side wall that extend vertically upward, respectively, from a third one and a fourth one of the plurality of base peripheral edges;
an opening defined by a plurality of top peripheral edges each formed by a different one of the first and the second end walls and the first and the second side walls and forming an opening footprint that fits within the base footprint;
the first and the second end walls being oriented parallel to one another, and the first and the second side walls being oriented so as to converge toward one another in a direction of the opening;
a plurality of internal vertical walls forming a plurality of medical device storage slots serially arranged between the first and the second end walls, each of the plurality of medical device storage slots extending horizontally from the first side wall to the second side wall and vertically between the opening and the base wall; and
the plurality of medical device storage slots further extending horizontally between the first and the second side walls and being shaped according to the convergence of the first and the second side walls so as to retain within the plurality of medical device storage slots a plurality of wound-up elongate medical devices inserted through the opening.

2. The medical device holder of claim 1 wherein a first inner surface of the first side wall tracks a first arc of a circle and a second inner surface of the second side wall tracks a second arc of the circle.

3. The medical device holder of claim 2 wherein the plurality of medical device storage slots define a common center axis that extends through a center point of the circle.

4. The medical device holder of claim 2 wherein each of the first side wall and the second side wall includes a lower section oriented perpendicular to the planar base face and an upper section that follows a curve of the circle.

5. The medical device holder of claim 4 wherein a third inner surface of the base wall forms a bottom of each one of the plurality of medical device storage slots and is oriented parallel to the planar base face.

6. The medical device holder of claim 4 wherein the opening footprint is oriented parallel to the base footprint.

7. The medical device holder of claim 6 wherein a number of the plurality of medical device storage slots is greater than three.

8. The medical device holder of claim 1 wherein the plurality of medical device storage slots are in fluidic communication with one another.

9. A medical device holder assembly comprising:
a holder including a one-piece holder body having a horizontally extending base wall with a plurality of base peripheral edges extending about a planar base face, a first end wall and a second end wall extending vertically upward, respectively, from a first one and a second one of the plurality of base peripheral edges, and a first side wall and a second side wall extending vertically upward, respectively, from a third one and a fourth one of the plurality of base peripheral edges;
the one-piece holder body further having a plurality of internal vertical walls forming a plurality of medical device storage slots extending between the first and the second side walls, and serially arranged between the first and the second end walls;
the one-piece holder body further having a plurality of top peripheral edges each formed by a different one of the first and the second end walls and the first and the second side walls and defining an opening to the plurality of medical device storage slots;
the first and the second end walls being oriented parallel to one another, and the first and the second side walls being oriented so as to converge toward one another in a direction of the opening; and
a plurality of elongate medical devices each wound in opposition to an internal unwinding bias and trapped in a biased state by way of contact with the first and the second side walls and the base wall within one of the plurality of medical device storage slots.

10. The medical device holder assembly of claim 9 further comprising a sterile envelope containing the medical device holder and the plurality of elongate medical devices.

11. The medical device holder assembly of claim 9 wherein the plurality of base peripheral edges form a first rectangular footprint, and the opening forms a second rectangular footprint that fits within the first rectangular footprint.

12. The medical device holder assembly of claim 9, wherein the plurality of medical device storage slots are in fluidic communication with one another.

13. The medical device holder assembly of claim 9, further comprising a base stabilizer operationally connected to the base wall.

14. The medical device holder of claim 13, wherein the base stabilizer forms a first footprint and the plurality of base peripheral edges forms a second footprint that fits within the first footprint.

15. A medical device holder comprising:
a one-piece holder body having a horizontally extending base wall with a plurality of base peripheral edges extending about a planar base face, a first end wall and a second end wall extending vertically upward, respectively, from a first one and a second one of the plurality of base peripheral edges, and a first side wall and a second side wall extending vertically upward, respectively, from a third one and a fourth one of the plurality of base peripheral edges;
the one-piece holder body further having a plurality of internal vertical walls each extending from the first side wall to the second side wall and forming a plurality of storage slots serially arranged between the first and the second end walls for storing a plurality of medical devices;
the one-piece holder body further having a plurality of top peripheral edges each formed by a different one of the first and the second end walls and the first and the second side walls and defining an opening to the plurality of storage slots; and
the first and the second end walls being oriented parallel to one another, and the first and the second side walls being oriented so as to converge toward one another in a direction of the opening.

16. The medical device holder of claim 15 wherein the plurality of storage slots are in fluidic communication with one another.

17. The medical device holder of claim 16 wherein the plurality of internal vertical walls each include a bottom edge, and a plurality of gaps providing the fluidic communication are formed between the bottom edges and the base wall.

* * * * *

UNITED STATES PATENT AND TRADEMARK OFFICE
CERTIFICATE OF CORRECTION

| | | |
|---|---|---|
| PATENT NO. | : 11,219,499 B2 | Page 1 of 1 |
| APPLICATION NO. | : 16/404258 | |
| DATED | : January 11, 2022 | |
| INVENTOR(S) | : Mitchell Kenneth Czapla and Matthew Christopher Nodley | |

It is certified that error appears in the above-identified patent and that said Letters Patent is hereby corrected as shown below:

On the Title Page

Item (73) The Assignee listed as:
M2 Medical Solutions, LLC 188 N Avon Ave. Suite 101, Avon, IN 46123.
Should read:
M2 Medical Solutions, Inc. 4160 Cairo Way, Avon, IN 46123.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*